United States Patent [19]
Harrison et al.

[11] Patent Number: 6,057,117
[45] Date of Patent: May 2, 2000

[54] IDENTIFICATION AND USE OF SELECTIVE INHIBITORS OF GLYCOGEN SYNTHASE KINASE 3

[75] Inventors: Stephen D. Harrison, Berkeley; David B. Ring, Palo Alto, both of Calif.

[73] Assignee: Chiron Corporation, Emeryville, Calif.

[21] Appl. No.: 09/267,971

[22] Filed: Mar. 12, 1999

Related U.S. Application Data

[63] Continuation of application No. 08/832,567, Apr. 2, 1997
[60] Provisional application No. 60/014,871, Apr. 4, 1996, abandoned.

[51] Int. Cl.$^7$ ..................................................... G01N 33/53
[52] U.S. Cl. .............................. 435/7.93; 435/4; 435/7.1; 435/7.92; 435/194; 435/287.2; 514/1; 514/2
[58] Field of Search ................................ 514/1, 2; 435/4, 435/7.1, 7.92, 7.93, 194, 287.2

[56] References Cited

U.S. PATENT DOCUMENTS 5,252,333  10/1993  Horrobin ................................. 424/422

FOREIGN PATENT DOCUMENTS

| | | |
|---|---|---|
| 0 616 032 A3 | 3/1994 | European Pat. Off. . |
| WO 91/02085 | 8/1990 | WIPO . |
| WO 96/25949 | 1/1996 | WIPO . |
| WO 97/18303 | 11/1996 | WIPO . |
| WO 97/22360 | 12/1996 | WIPO . |
| WO 97/41854 | 4/1997 | WIPO . |
| WO 98/16528 | 10/1997 | WIPO . |
| WO 97/41854 | 11/1997 | WIPO . |

OTHER PUBLICATIONS

Wang et al. (1994) Analytical Biochem. 220, pp. 397–402, 1994.
Anderton et al., "Modulation of PHF–Like tau Phosphorylation in Cultured Neurones and Transfected Cells", *Neurobiology of Aging* 16(3):389–402, 1995.
Borthwick et al., "Inhibition of Glycogen Synthase Kinase–3 by Insulin in Cultured Human Skeletal Muscle Myoblasts", *Biochemical and Biophysical Research Communications* 210(3):738–745, May 25, 1995.
Huang et al., "Glucose–6–P Control of Glycogen Synthase Phosphorylation in Yeast", *The Journal of Biological Chemistry*, vol. 272, No. 36, Sep. 5, 1997, pp. 22495–22501.
Ishiguro et al., "Glycogen Synthase Kinase 3β is Identical to Tau Protein Kinase I Generating Several Epitopes of Paired Helical Filaments", FEBS 12596 Lett, Jul. 1993, pp. 167–172.
Ishiguro et al., Chemical Abstract No. 126:291921, "Advances in Neurological Sciences," No. 212, vol. 41, No. 1, Feb. 1997.
Klein and Melton, "A Molecular Mechanism for the Effect of Lithium on Development", *Proc. Natl. Acad. Sci. USA* 93:8455–8459, Aug., 1996.
Latimer et al., "Stimulation of MAP Kinase by v–raf Transformation of Fibroblasts Fails to Induce Hyperphosphorylation of Transfected tau", *FEBS Letters* 365:42–46, 1995.
Lovestone et al., "Alzheimer's Disease–Like Phosphorylation of the Microtubule–Associated Protein tau by glycogen Synthase Kinase–3 in Transfected Mammalian Cells", *Current Biology* 4(12):1077–1086, 1994.
Massillon et al., "Identification of the Glycogenic Compound 5–Iodotubercidin as a General Protein Kinase Inhibitor", *Biochem J.* 299:123–128, 1994.
Pugazhenthi et al., "Regulation of Glycogen Synthase Activation in Isolated Hepatocytes", *Molecular and Cellular Biochemistry*, 149/150:95–101, 1995.
Saran, "Antidiabetic Effects of Lithium" *J. Clin. Psychiatry* 43(9):383–384, Sep., 1982.
Sperber et al., "Glycogen Synthase Kinase–3β Phosphorylates tau Protein at Multiple sites in Intact Cells" *Neuroscience Letters* 197:149–153, 1995.
Stambolic et al., "Lithium Inhibits Glycogen Synthase Kinase–3 Activity and Mimics Wingless Signalling in Intact Cells" *Current Biology* 6(12):1664–1668, 1996.
Sutherland et al., "Inactivation of Glycogen Synthase Kinase–3β by Phosphorylation: New Kinase Connections in Insulin and Growth–Factor Signalling" *Biochem. J.* 196:15–19, 1993.
Takashima et al., "Amyloid β Peptide Induces Cytoplasmic Accumulation of Amyloid Protein Precursor via tau Protein Kinase I/glycogen Synthase Kinase–3β in rat Hippocampal Neurons" *Neuroscience Letters* 198:83–86, 1995.
Takashima et al., "Exposure of rat hippocampal Neurons to Amyloid β Peptide (25–35) Induces the Inactivation of Phosphatidyl Inositol–3 Kinase and the Activation of tau Protein Kinase I/glycogen Synthase Kinase–3β" *Neuroscience Letters* 203:33–36, 1996.
Takashima et al., "tau Protein Kinase I is Essential for Amyloid β–Protein–Induced Neurotoxicity", *Proc. Natl. Acad. Sci., USA* 90:7789–7993, Aug. 1993.
Lovestone et al. (1994) Current Biol. 4/12, pp. 1077–1086.
Latimer et al. (1995) FEBS Letters 365, pp. 42–46.
Song et al. (1995) J. Protein Chem. 14/2, pp. 95–105.
Cross et al. (1995) Nature 378, pp. 785–789.
Fiol et al., "Ordered Multisite Protein Phosphorylation", The Journal of Biological Chemistry, vol. 265, No. 11, pp. 6061–6065 (1990).
Hegazy et al., "Inhibition of Glycogen Synthase Kinase 3 by Polycations", 72nd Annual Meeting of the Federation of American Societies for Experimental Biology, Las Vegas, Nevada, USA, May 1–5, 1988, FASETS (Fed. Am. Soc. Exp. Biol.) J2(4) 1988, Abstract.

(List continued on next page.)

*Primary Examiner*—Rebecca E. Prouty
*Assistant Examiner*—Enrique D. Longton
*Attorney, Agent, or Firm*—Sharon M. Fujita; David P. Lentini; Robert P. Blackburn

[57] ABSTRACT

The invention provides for use of selective inhibitors of GSK3 for treatment of diseases that are mediated by GSK3 activity, including non-insulin dependent diabetes mellitus (NIDDM) and Alzheimer's disease. Also described are methods of identifying inhibitors of GSK3 activity. The selective GSK3 inhibitor can be a peptide, peptoid, small organic molecule, or polynucleotide.

11 Claims, No Drawings

OTHER PUBLICATIONS

Baum et al., "Overexpressed tau protein in cultured cells is phosphorylated without formation of PHF: implication of phosphoprotein phosphatase involvement", 1995, Molecular Brain Research, 34:1–17.

Ciudad et al., "Control of glycogen synthase phosphorylation in isolated rat hepatocytes by epinephrine, vasopressin and glucagon", 1984, J Biochem., 142:511–520.

Cross et al., "The inhibition of glycogen synthase kinase–3 by insulin or insulin–like growth factor 1 in the rat skeletal muscle cell line L6 is blocked by wortmannin, but not by rapamycin: evidence that wortmannin blocks activation of the mitogen–activated protein kinase pathway in L6 cells between Ras and Raf", 1994, J. Biochem., 303:21–26.

Hegazy et al., "Inhibitory effect of polycations on phophorylation of glycogen synthase by glycogen synthase kinase 3", 1989, BBA, 1011:198–204.

Hiken et al., "Rat skeletal muscle glycogen synthase: Phosphorylation of the purified enzyme by cAMP–dependnet and independent protein kinases", 1985, Archives of Biochemistry and Biophysics, 236:59–71.

Hoshi et al., "Regulation of mitochondrial pyruvate dehyrogenase activity by tau protein kinase I/glycogen synthase kinase 3β in brain" 1996, Proc. Natl. Acad. Sci. USA, 93:2719–2723.

Imazu et al., "Phosphorylation and inactivation liver glycogen synthase by liver protein kinases" 1984, Journal of Biological Chemistry, 259(3):1813–1821.

Lawrence et al., "Control of glycogen synthase by insulin and isoproterenol in rat adipocytes", 1986, Journal Biological Chemistry, 261(2):669–677.

Lint et al. "A specific immunoprecipitation assay for the protein $F_A$/glycogen synthase kinase $3^1$", 1993, Analytical Biochemistry, 208:132–137.

Liu et al., "The state of phosphorylation of normal adult brain τ, fetal τ and τ from alzheimer paired helical filaments at amino acid residue $ser^{262}$", 1996, Journal of Neurochemistry, 1131–1139.

Mandelkow et al., "Tau domains, phosphorylation, and interactions with microtubules" 1995, Neurobiology of Aging, 16(3):355–363.

Nitsch et al., "Alzheimer's disease amyloid precursor proteins, signal transduction, and neuronal transplantation" 1993, Annals of the New York Academy of Sciences, 695:209–216.

Singh et al., "Differential phosphorylation of human tau isoforms containing three repeats by several protein kinases" 1996, Archives of Biochemistry and Biophysics, 328(1):43–50.

Takahashi et al., "Localization and developmental changes of τ protein kinase I/glycogen synthase kinase–3β in rat brain" 1994 Journal of Neurochemistry, 245–255.

Wang et al., "Use of a synthetic peptide as a selective substrate for glycogen synthase kinase3", 1994, Analytical Biochemistry, 220:397–402.

Wang et al., "Inactivation of rabbit muscle glycogen synthase by glocogen synthase kinase–3", 1993, J. Biol. Chem., 268(32):23876–23880.

Weber, "Advances in enzyme regulation", 1983, Pergamon Press, 21:322–330.

Yang et al., "Synergistic control mechanism for abnormal site phosphorylation of alzheimer's diseased brain tau by kinase $F_A$/GSK–3α", 1993, Biochemical and Biophysical Research Communications, 197(2):400–406.

Yang et al., "Protein kinase $F_A$/GSK–3 phosphorylates τ on $ser^{235}$ –pro and $ser^{404}$ –pro that are abnormally phosphorylated in alzheimer's disease brain", 1993, Journal of Neurochemistry, 1742–1747.

Zhang et al., "Mechanisms of multisite phosphorylation and inactivation of rabbit muscle glycogen synthase", 1993, Archives of Biochemistry and Biophysics, 304:219–225.

IDENTIFICATION AND USE OF SELECTIVE INHIBITORS OF GLYCOGEN SYNTHASE KINASE 3

CROSS-REFERENCE TO RELATED APPLICATIONS

This application is a Continuation of application Ser. No. 08/832,567, filed Apr. 2, 1997, which application(s) are incorporated herein by reference.

This patent application claims the benefit of U.S. Provisional Application Serial No. 60/014,871, filed Apr. 4, 1996, now abandoned, the specification of which is hereby incorporated by reference.

FIELD OF THE INVENTION

This invention provides materials and methods relating to identification of selective inhibitors of glycogen synthase kinase 3 (GSK3), and also concerns methods of treating a condition mediated by GSK3 activity by administrating a selective inhibitor of GSK3. The biological conditions treatable include non-insulin dependent diabetes mellitus and Alzheimer's disease.

BACKGROUND OF THE INVENTION

Glycogen synthase kinase 3 (GSK3) is a proline-directed serine/threonine kinase originally identified as an activity that phosphorylates glycogen synthase as described in Woodgett, *Trends Biochem Sci*, 16: 177–181 (1991). GSK3 consists of two isoforms, $\alpha$ and $\beta$, and is constitutively active in resting cells, inhibiting glycogen synthase by direct phosphorylation. Upon insulin activation, GSK3 is inactivated, thereby allowing the activation of glycogen synthase and possibly other insulin-dependent events. Subsequently, it has been shown that GSK3 is inactivated by other growth factors or hormones that, like insulin, signal through receptor tyrosine kinases. Examples of such signaling molecules include IGF-1 and EGF as described in Saito et al, *Biochem J*, 303: 27–31 (1994), Welsh et al, *Biochem J*, 294: 625–629 (1993), and Cross et al, *Biochem J*, 303: 21–26 (1994). GSK3 has been shown to phosphorylate $\beta$-catenin as described in Peifer et al, *Develop Biol* 166:543–56 (1994). Other activities of GSK3 in a biological context include GSK3's ability to phosphorylate tau protein in vitro as described in Mandelkow and Mandelkow, *Trends in Biochem Sci* 18: 480–83 (1993), Mulot et al, *Febs Lett* 349: 359–64 (1994), and Lovestone et al, *Curr Biol* 4: 1077–86 (1995), and in tissue culture cells as described in Latimer et al, *Febs Lett* 365: 42–6 (1995). Selective inhibition of GSK3 may be useful to treat or inhibit disorders mediated by GSK3 activity.

SUMMARY OF THE INVENTION

The invention is a method for treating a biological condition mediated by GSK3 activity by administering an effective amount of a pharmaceutical composition comprising a selective GSK3 inhibitor to a subject having a condition mediated by GSK3 activity or susceptible to such a condition. The biological condition can be, for example, non-insulin dependent diabetes mellitus (NIDDM) or Alzheimer's disease. The selective inhibitor of GSK3 activity can be a small organic molecule, a peptide, a peptoid, or a polynucleotide. The method can include administration of a second therapeutic agent, for example, lithium ion. The invention is also an in vitro method of identifying an inhibitor of GSK3 kinase activity. A candidate inhibitor can be a peptide, a peptoid, a small organic molecule, or polynucleotide. The invention thus provides a pharmaceutical composition comprising an inhibitor identified by this in vitro method.

The invention is also a transgenic fruit fly having a transgene encoding a GSK3 inhibitory polypeptide, for example p110*, under the regulatory control of an eye specific promoter, where the transgenic fruit fly exhibits an enhanced rough eye mutant morphology. The invention provides a method of screening for an inhibitor of GSK3 activity by administering to this transgenic fruit fly a candidate inhibitor of GSK3, and identifying a functional inhibitor by its ability to enhance a rough eye mutant morphology.

The invention provides a pharmaceutical composition for treating a condition mediated by GSK3 activity having a pharmaceutically acceptable carrier and an effective amount of a selective inhibitor of GSK3 activity. The invention also provides a method of treating a subject having NIDDM or Alzheimer's disease by administering this pharmaceutical composition to the subject, a method of promoting activation of an insulin signaling pathway by contacting a cell characterized by insulin resistance with an effective amount of a selective inhibitor of GSK3, and a method of reducing tau hyperphosphorylation and polymerization in a population of cells exhibiting tau polymerization by contacting said cells with an effective amount of a selective inhibitor of GSK3. The selective inhibitor of GSK3 used in these methods can be a small molecule.

DETAILED DESCRIPTION

All patents, patent publications, and scientific articles cited herein are incorporated by reference.

This invention provides materials and methods for identifying inhibitors of the proline directed serine/threonine kinase GSK3. The invention also provides for use of selective inhibitors of GSK3 to treat biological conditions mediated by GSK3 activity, for example, Alzheimer's disease (AD) and non-insulin dependent diabetes mellitus (NIDDM).

Screening Assays

The screening assays described herein can be used to screen for selective inhibitors of GSK3. A selective inhibitor of GSK3 is an inhibitor that inhibits GSK3 at a much lower concentration of inhibitor than that required for any inhibitory effect on any other kinases. Other kinases are tested in comparison to GSK3 related assays that are used to identify the GSK3 inhibitor being tested for selectivity. Preferably, the GSK3 inhibitor selectively inhibits GSK3 and does not appreciably inhibit any other kinase.

Currently there are no known high throughput screening assays for inhibitors of GSK3. To address this problem, the inventors have developed methods for identifying these inhibitors. The methods include methods to assay for GSK3 kinase activity in an in vitro assay, in a cell-based assay, in a binding assay, and an in vivo Drosophila assay. Additionally, the inventors use assays specific for GSK3 in NIDDM, including assays using stable tissue culture cells, assays using differentiated cell lines, and assaying using human muscle primary myocytes.

A. In Vitro Kinase Assay

General aspects of the kinase activity assays are conducted as described in U.S. Pat. No. 4,568,649 EP 0154,734, and JP 84/52452, incorporated by reference in full. These references describe kinase activity assays conducted for kinases other than GSK3. Many of the components of the in vitro kinase assay can also be used in the other assays for identifying selective inhibitors of GSK3.

The in vitro assay provides a high throughput method for screening for selective inhibitors that act on the polypeptide GSK3 and is suitable for an initial screen of candidate inhibitors. First the assay can be conducted for GSK3 inhibition as compared to a control reaction in the absence of a candidate inhibitor. To provide information as to whether the GSK3 inhibition identified is selective for GSK3, any positive inhibitors so identified can then also be tested for their potential to inhibit other kinases, including kinases that are close in structure and mode of action to GSK3, and those kinases that are distant from GSK3 in structure and mode of action. Any kinases can be used for this comparative purposes, for example the known kinases CDC2, p70S6 kinase, Akt kinase, cAb1, cSRC, and PI 3-kinase. Selective inhibition of GSK3 is identified where the IC50 of an inhibitor for GSK3 is substantially lower than the IC50 of the same inhibitor for another kinase tested in a related assay. The IC50 is that concentration of inhibitor that inhibits 50% of the enzyme activity (for example GSK3 activity or the activity of another kinase). That is, the concentration of inhibitor that reduces the enzyme activity to 50% of normal. Preferably the IC50 of the inhibitor of GSK3 is at least 10 fold lower than the IC50 for any other kinases tested for that inhibitor to be identified as a selective inhibitor of GSK3. For example, the IC50 of a candidate inhibitor can be 1 nM for GSK3 inhibition and 10 nM or greater for effecting inhibition of any of the other kinases tested.

The term "glycogen synthase kinase 3" or "GSK3" as used herein refers to GSK3α or GSK3β. GSK3 is a protein originally identified by its phosphorylation of glycogen synthase as described in Woodgett et al, *Trends Biochem Sci*, 16: 177–181 (1991). Synonyms of GSK3 are tau protein kinase I (TPK I), FA kinase and kinase FA. Mammalian forms of GSK3 have been cloned as described in Woodgett, *EMBO J.* 9(8): 2431–2438 (1990), and He et al, *Nature* 374: 617–22 (1995) and Stambolic and Woodgett, *Biochem. J.* 303: 701–704 (1994). Inhibitors of GSK3 can be inhibitors of any of the known forms of GSK3, including either GSK3α or GSK3β or both. GSK3 polypeptide as used herein includes the native protein and also can further include truncations, variants, alleles, analogs and derivatives of a native GSK3 protein. Such polypeptides possess one or more of the bioactivities of the GSK3 protein, including kinase activities such as polymerizing tau protein, or phosphorylating glycogen synthase, for example. Thus, GSK3 polypeptides from which inhibitors are screened can have sequence identity of at least 40%, preferably 50%, preferably 60%, preferably 70%, more preferably 80%, and most preferably 90% to the amino acid sequence of the native protein, wherever derived, from human or nonhuman sources. The polynucleotides encoding a GSK3 polypeptide can have 60%, preferably 70%, more preferably 80%, more preferably 90% and most preferably 95% sequence identity to a native polynucleotide sequence of GSK3. Also included, therefore, are alleles and variants of the native polynucleotide sequence so that the polynucleotide encodes an amino acid sequence with substitutions, deletions, or insertions, as compared to the native sequence.

The term "peptide substrate" refers to a peptide or a polypeptide or a synthetic peptide derivative that can be phosphorylated by GSK3 activity in the presence of an appropriate amount of ATP or a phosphate donor. Detection of the phosphorylated substrate is generally accomplished by the addition of a labeled phosphate that can be detected by some means common in the art of labeling, such as radiolabeled phosphate. The peptide substrate may be a peptide that resides in a molecule as a part of a larger polypeptide, or may be an isolated peptide designed for phosphorylation by GSK3.

Additionally, a synthetic peptide substrate designed for a purpose appropriate to the assay can be used, for example the CREB peptide. CREB peptide is a sequence within the CREB DNA-binding protein. See Wang et al, *Anal. Biochem* 220: 397–402 (1994). The inventors provide a novel modification of this peptide substrate. Peptide substrates that are phosphorylated by GSK3 have in common the amino acid motif SXXXS (SEQ ID NO. 2) where S is serine and X is any amino acid, and where the N terminal S is the target of phosphorylation by GSK3, and the C terminal S is prephosphorylated. Such peptides are appropriate peptide substrates for GSK3 activity assays and can be synthetically made by standard techniques.

The term "prephosphorylated" refers to phosphorylating a substrate with non-radiolabeled phosphate in advance of conducting a kinase assay using the substrate. Generally, the substrate that is used for a kinase activity assay will contain one or more sites that are phosphorylatable by the kinase being tested, and may contain one or more other phosphorylatable sites that are not specific for the kinase being tested. These other sites need to be phosphorylated in order to create a phosphorylatable motif for the kinase being tested. Thus, before conducting the kinase assay, it may be beneficial or required to phosphorylate a specific phosphorylatable site on the substrate, for example, the C terminal serine of the motif SXXXS (SEQ ID NO. 2), with non-labeled phosphate in advance of running the kinase assay. The prephosphorylation can be performed synthetically.

An example of a prephosphorylated substrate in the context of an assay of the invention is an anchor ligand such as biotin attached to the sequence of the CREB peptide SGSGKRREILSRRPSYR (SEQ ID No. 1) where the S near the C terminal between P and Y is prephosphorylated and the S between L and R is phosphorylatable by GSK3 during a kinase assay. The purpose of the prephosphorylation is that GSK3 phosphorylation motif requires prephosphorylation at the final S of the motif SXXXS (SEQ ID No. 2) (reading N terminal to C terminal) in order for the more N-terminal S to become phosphorylatable by GSK3.

In the in vitro kinase assay and in some of the other assays for inhibitors of GSK3, recombinant GSK3 or endogenous GSK3 is combined with a peptide substrate and a candidate inhibitor. The peptide substrate is selected or designed as is appropriate to the particular assay. For example, where inhibition of GSK3 activity with respect to phosphorylation of glycogen synthase is sought, a glycogen synthase polypeptide, or polypeptide derivative of glycogen synthase might be most appropriate. Where inhibition of phosphorylation of tau protein is sought, a peptide substrate that is the tau polypeptide, or a derivative of the tau polypeptide, might be most appropriate. Other potential and exemplary peptide substrates of GSK3 can be designed from c-Jun and β-catenin.

An "anchor ligand" refers to a ligand that is attachable to a peptide substrate (for example the peptide substrate of formula SXXXS (SEQ ID NO. 2)) that can bind a substrate anchor (defined below). The purpose of the anchor ligand is to anchor the peptide substrate to an anchor from which it is possible to detect whether the peptide substrate has been phosphorylated with a labeled phosphate. Thus, the substrate anchor and an anchor ligand ensure that the peptide substrate, labeled or not, does not get washed from the assay, so that those peptide substrate molecules that have been labeled can be detected and quantified. An example of an anchor ligand is biotin, where the substrate anchor is streptavidin agarose beads impregnated with scintillant or scintillant-lined streptavidin coated wells.

A "substrate anchor" refers to a molecule that is affixed to, for example, an agarose bead, or the inside of a microwell of a multiwell plate, and that can bind an anchor ligand with high affinity. The anchor ligand will generally be covalently or otherwise attached to a peptide substrate. An example of a substrate anchor is streptavidin agarose beads impregnated with scintillant or scintillant-lined streptavidin coated wells, where the anchor ligand is biotin. Typically, the agarose bead or the microwell will contain a material that scintillates in the presence of a radiolabeled material, so that a substrate anchor that binds an anchor ligand attached to a peptide substrate with a radiolabeled phosphorylation site can cause the scintillant material to react to the proximity of the radiolabeled phosphate. This reaction is quantifiable and indicates the presence of a labeled substrate, and so the presence of active GSK3.

GSK3 isoforms α and β phosphorylate serine and threonine residues in the amino acid motif serine-proline (SP) or threonine-proline (TP), as well as at the N-terminal serine in the motif SXXXS (SEQ ID NO. 2), provided that the C-terminal serine in this sequence is prephosphorylated, as described in Wang et al, *Anal Biochem* 220: 397–402 (1994) and Roach, *J Biol Chem* 266: 14139–42 (1991). The assay published in Wang et al, is a low throughput GSK3 assay that makes use of a peptide substrate whose sequence is based on that of a GSK3 phosphorylation site in the CREB DNA-binding protein. In the published assay, the C-terminal serine in the SXXXS (SEQ ID NO. 2) motif is prephosphorylated by casein kinase II. The inventors herein have developed a modified peptide of motif SXXXS (SEQ ID NO. 2) that can be synthesized with the C-terminal serine prephosphorylated (Chiron Mimotopes, Clayton, Australia) and which also contains an N-terminal anchor ligand. The novel peptide substrate, so designed and constructed with an anchor ligand is then able to accomplish binding to a substrate anchor at the N-terminal anchor ligand. This novel process eliminates the need to prephosphorylate the C-terminal serine as a separate step, and facilitates high throughput screening. A substrate anchor is some molecule or mechanism for keeping the substrate present during a wash. For example, where the anchor ligand is biotin, especially in the case where the peptide substrate is bound at the N-terminus to biotin, the anchor can be a molecule that binds biotin, for example, streptavidin.

The in vitro method of identifying an inhibitor of GSK3 activity includes constructing a peptide substrate. The peptide substrate can be any peptide substrate phosphorylatable by GSK3, and may be a peptide substrate including the formula: anchor ligand-SXXXS (SEQ ID NO. 2) (where X is any amino acid) prephosphorylated at C terminal S, and contacting the prephosphorylated substrate with GSK3 in the presence of radiolabeled phosphate-γATP, a substrate anchor, and a candidate inhibitor. The in vitro method of identifying an inhibitor of GSK3 kinase activity includes contacting a peptide substrate coupled to an anchor ligand with GSK3 polypeptide in the presence of radiolabeled phosphate-γATP, a substrate anchor, and a candidate inhibitor, measuring an incorporation of radiolabel into the peptide substrate, then, in a separate assay vessel contacting a peptide substrate coupled to an anchor ligand with GSK3 in the presence of radiolabeled phosphate-γATP, and a substrate anchor, and measuring an incorporation of radiolabel into said peptide substrate; ultimately an inhibitor of GSK3 kinase activity is identified by a reduction of label incorporation in the assay with the candidate inhibitor as compared to the assay without the candidate inhibitor. The inhibition of GSK3 kinase activity can be identified by a reduction in labeling of substrate relative to control. The degree of phosphorylation of the peptide substrate is monitored by assaying the incorporation of radioactive phosphate into the peptide substrate. Inhibition of this incorporation is an indication of inhibition of GSK3, as compared to a control reaction conducted in the absence of a candidate inhibitor. Alternatively, the GSK3 activity is measured by indirectly observing phosphorylation of a coexpressed substrate, for example by mobility shift on an SDS gel or by using phosphoform specific antibodies. Another alternative is to measure physiological consequence of GSK3 inhibition by, for example measuring glycogen synthase activation or β-catenin accumulation.

To conduct the in vitro kinase assay of the invention using microwells, scintillant may be present by pre-coating the wells with a scintillant material, or by adding it later following a wash step. The scintillant can be purchased from Packard, Meriden, Conn. Wells coated with scintillant are then in addition coated with streptavidin. Where the scintillant is added later, the streptavidin can be present on agarose beads. In any event, the streptavidin in the wells binds the biotin that contacts it. Where the substrate anchor is biotin, the radiolabel on the phosphorylated substrate that has been conjugated to the biotin will cause the scintillant to emit light. Where the streptavidin is attached to agarose beads containing scintillant, binding a biotin-conjugated radiolabeled peptide substrate will cause the beads to scintillate and will be an indication of the inhibitory activity of the candidate inhibitor, as compared to a control. In both the case of the wells lined with the scintillant, and the agarose beads containing scintillant, a reduction in scintillation as compared to a control amount of scintillation measured under non-inhibitory conditions, indicates the presence of a functional inhibitor of GSK3 activity. If the peptide has been phosphorylated by GSK3 with $^{32}$P-labeled or $^{33}$P-labeled phosphate, radioactive decay will cause the scintillant present in a microwell or mixed in agarose beads that are present in the reaction mixture to emit light and the measure of the amount of light emitted will be a measure of the activity of GSK3 in the assay. Low activity of GSK3 observed in the presence of a candidate inhibitor, as compared to the activity of GSK3 in the absence of the inhibitor, may indicate that the inhibitor is functional and can inhibit GSK3 kinase activity. In any case, an equal amount of streptavidin should be loaded into each well or should be affixed to the agarose beads, and an equal amount of the beads should be added to each assay.

B. Cell-Based Assays

Several cell-based assays can be used to screen for inhibitors that can penetrate a cell and can act within the cell at any step in the process of expression or activity of GSK3. Thus, a cell-based assay can screen for those inhibitors that act during transcription of GSK3 or that can act during intracellular post-transcriptional events in the process of making mature GSK3, in addition to those that can inhibit GSK3 kinase or binding activity. A cell-based assay includes a cell that can express GSK3, such as a cell transformed with the gene encoding GSK3 including also regulatory control sequences for the expression of the gene, or a cell that expresses GSK3 endogenously. The cell capable of expressing GSK3 is incubated in the presence of a candidate inhibitor. GSK3 from the cell is placed in contact with a peptide substrate, and radiolabeled phosphate-ATP. The amount of phosphorylation of the peptide substrate is an indication of the degree of inhibition accomplished by the candidate inhibitor, as compared to a control.

The cell-based method of identifying a GSK3 inhibitor can include use of a peptide substrate, for example a peptide substrate of formula: anchor ligand-SXXXS (SEQ ID NO. 2), prephosphorylated at C terminal S, where X is any amino acid, and radioactive labeled phosphate-γATP, and identifying inhibition of GSK3 activity by a reduction in labeling of substrate, as compared to a control.

C. Binding Assays

A binding assay can be used for identification of molecules that inhibit GSK3 binding to other molecules. Such identification can act as an initial screen of candidate inhibitors of GSK3 kinase activity because GSK3 kinase activity may include binding to a phosphorylatable target or other molecule. Identification of GSK3 inhibitory molecules can be conducted by screening for those molecules that can inhibit binding of GSK3 to a potential substrate, including, for example, glycogen synthase or tau protein. The term "binding activity" in reference to interaction between two molecules indicates a higher affinity binding and a lower dissociation constant than non-specific binding, thus distinguishing specific binding activity from background binding. An inhibitor functional in a binding assay would be expected to inhibit the binding of GSK3 to a substrate, and thus might be expected to bind competitively to GSK3 or its substrate. Where the peptide substrate is used to conduct a binding assay, the presence of an inhibitor is monitored by the interruption of binding of the substrate to GSK3 as compared to a control reaction in the absence of a candidate inhibitor.

D. Drosophila Screening Assay

An alternative or subsequent assay that can be used to screen in vivo for inhibitors of GSK3 kinase activity is a Drosophila eye screen for inhibitors. The fly eye screen detects inhibitory activity by expressing, under control of an eye specific promoter, a polypeptide that can effect a reduction in GSK3 activity, either by direct or indirect action on endogenous GSK3 in the fly eye cells. For example, such a polypeptide can be p110* polypeptide. P110* is effectively inhibitory of GSK3, although its method of action is believed to be by activation of the kinase Akt that then phosphorylates GSK3, making GSK3 inactive. By reducing the activity of endogenous GSK3, expression of a GSK3 inhibitory polypeptide or a polypeptide with an indirect inhibitory effect like p110*, sensitizes the assay so that lower concentrations of candidate inhibitor can be tested. The p110* polypeptide is a fusion mutant derived from phosphotidylinositol 3-kinase (PI 3-kinase) and is described in Hu et al, *Science,* 268:100–102 (1995). In addition, the p110* polypeptides can be targeted to the cell membrane such as those mutants described in Klippel et al, *Mol. Cell. Biol.* 16(8): 4117–4127 (1996). The eye specific promoter can be any promoter specific to expression of proteins in eye tissue, including but not limited to, for example, GMR as described in Hay et al, *Development* 120: 2121–9 (1994), and the sevenless promoter, as described in Bowtell et al, *Genes and Development* 2: 620–634 (1988). Expression of GSK3 with p110* results in a mutant morphology called roughening or rough eye mutant morphology.

Drosophila embryos are transformed by the method of Karess and Rubin, *Cell* 38:135–146 (1984) with a polynucleotide construct made up of a GSK3 inhibitory polypeptide coding sequence under the regulatory control of a GMR promoter. The preferred polynucleotide encoding is a polynucleotide encoding p110*, or a membrane-targeted version of p110*. The flies are allowed to develop normally and are selected by eye morphology for successful transformants. Successful transformants will have an aberrant morphology characterized by rough eye cell morphology that is detectable under a dissecting microscope. The transgenic flies are then fed food spiked with an appropriate dose of a candidate inhibitor. The amount of the inhibitor will depend on the desired potency of the molecule as an inhibitor. The flies can be fed different small molecule inhibitors, for example, a different inhibitor for each population of transformants. The flies are fed a candidate inhibitor throughout third instar larval development during which time they are observed for enhancements of their rough eye mutant morphology. Positives are identified. This screening method may also be applied as a secondary or tertiary screen using candidate inhibitors that have already been found positive in prior screens such as the kinase or binding assay screening protocols. Variations to the protocol include injecting a candidate inhibitor into the third instar larvae of the transformants, which are then observed for a reversion of the rough eye morphology to normal.

The advantages of the Drosophila assay are that the assay can give initial in vivo data indicating whether the selective GSK3 inhibitor can inhibit in vivo, whether the inhibitor is toxic to an insect, whether the inhibitor is cell permeable, and whether the inhibitor is stable in an animal cell.

E. Cell-Based Assays Related to GSK3 in NIDDM

Assays designed for finding inhibitors of GSK3 in the context of NIDDM are based on two premises: that GSK3 inhibitors will potentiate insulin signaling by activating glycogen synthase (GS) and increasing glycogen synthesis and that stimulation of glycogen synthesis by GSK3 inhibitors will lead to increased uptake of glucose in NIDDM patients. The following assays test the ability of inhibitors of GSK3 to potentiate insulin-stimulated GS activity in tissue culture cells, and can ultimately be used to investigate the effect of these inhibitors on glucose uptake into cells.

In these assays measurement of the effectiveness of a given inhibitor is accomplished by the effect of inhibitors on glycogen synthase activity as described in Thomas et al, *Anal. Biochem.* 25:486–99 (1968), glucose uptake as described in Begun and Ragolia *Endocrinology* 137: 2441–6 (1996), Claraldi et al, *J. Clin. Invest.* 96:2820–27 (1995), Hara et al, *PNAS* 91:7415–19 (1994), Robinson and James, *Am. J. Physiol.* 263:E383–93(1992), and Sasoaka et al, *JBC* 270: 10885–92 (1995) and glucose incorporation into glycogen as described in Begun and Ragolia *Endocrinology* 137: 2441–6 (1996), Sasoaka et al, *JBC* 270: 10885–92 (1995), and Takata et al, *JBC* 267:9065–70 (1992).

1. Assays Using Stable Tissue Culture Cells a. Glucose Uptake and Glycogen Synthesis Assays for glucose uptake and glycogen synthesis can be conducted as described for cell-based assays generally. To measure glucose uptake and glycogen synthesis, a variety of stable tissue culture cell lines that respond to insulin stimulation by increasing the synthesis of glycogen and increasing the rate of glucose uptake from the medium can be used. These include HepG2 liver cells, CHO-IR cells, and Hirc cells. Under appropriate conditions the addition of insulin and glucose to HepG2 cells stimulates glycogen synthase activity and this stimulation is potentiated in the presence of the GSK3 inhibitor iodotubercidin. The response of glucose uptake in these cells to insulin, glucose and inhibitor can be as much as six fold, and consequently this assay is useful to detect the ability of inhibitors to potentiate glycogen synthesis in cells.

Chinese hamster ovary cells over-expressing insulin receptor (CHO-IR) have been used to measure insulin-stimulated glucose uptake, as described in Hara et al, *PNAS* 91: 7415–9 (1994), and glycogen synthase activity as described in Sakaue et al, *JBC* 270: 11304–9 (1995). CHO-IR cells show up to a 2.5 fold increase in glycogen synthase activity in response to insulin and can be used instead as an alternative to HepG2 cells.

Rat-1 fibroblast cells over-expressing the insulin receptor (Hirc) have been used to measure insulin-stimulated glucose incorporation into glycogen as described in Sasaoka et al., *JBC* 270:10885–92 (1995) and Takata et al., *JBC* 267:9065–70 (1992).

b. Assays Testing Cell Permeability and Intracellular GSK3 Activity

If compounds fail to stimulate glucose uptake or glycogen synthase activity, they may be tested to see if the defect is in their ability to enter cells or in their ability to inhibit GSK3 under intracellular conditions (i.e. 3 mM ATP). An in vivo kinase assay using tau protein was designed for this purpose. The tau assay relies on the ability to observe direct consequences of GSK3 activity within a cell, without first having to purify the GSK3 from a cell lysate. The tau protein assay uses tau, a microtubule-associated protein that is also a GSK3 substrate. See Lovestone et al, *Current Biology* 4(12):1077–86 (1994), Anderton et al, *Neurobiology of Aging* 16(3): 389–97 (1995), Latimer et al, *FEBS Let* 365: 42–6 (1995), and Sperber et al, *Neurosci Let* 197: 149–53 (1995). When GSK3 is over-expressed in mammalian cells, tau becomes phosphorylated on characteristic serine residues and can then be detected by phosphoform specific antibodies such as AT8, an antibody specific for phosphorylated tau. Thus, in the presence of active GSK3, tau protein can be detected by both AT8 and a phosphate-independent antibody such as Tau-1, while if GSK3 activity is inhibited, only the phosphate-independent Tau- 1 antibody will detect tau on a western blot; see Stambolic et al, *Cur Biol* 6(12): 1664–8 (1996).

Other assays that test functional GSK3 also provide a further test of intracellular GSK3 activity. These assays rely on the ability to observe indirect consequences of GSK3 activity within cells. An example of such an assay involves β-catenin stabilization. Cellular GSK3 activity leads to the destabilization of cytosolic pools of β-catenin in certain types of cell. Consequently, inhibition of GSK3 results in β-catenin stabilization and accumulation, which can be detected on a western blot. For example, the addition of iodotubercidin (a kinase inhibitor that is a nonspecific non-selective GSK3 inhibitor) to Drosophila cells leads to β-catenin accumulation. Similarly, LiCl in the cell culture medium causes an increase in intracellular β-catenin levels as described in Stambolic et al, *Cur. Biol.* 6(12):1664–8 (1996).

2. Assays Using Differentiated Cell-Lines

Assays using differentiated cell-lines can be conducted as described generally for cell-based assays. Insulin-stimulated uptake of glucose from the bloodstream is mostly performed by fat and muscle cells. Because different cell lines respond differently to glucose (e.g. liver cells have much higher insulin-independent glucose transport) examination of the effect of any GSK3 inhibitor in differentiated fat and muscle cells is important. These are less convenient cells to work with because they need to be exposed to differentiating conditions, sometimes for several weeks, before they can be used in assays. Consequently, the assays with differentiated cell-lines are to test compounds that potentiate insulin signaling in the earlier cell-based assays.

NIH 3T3-L1 adipocytes display the expected properties of a differentiated fat cell: they are mitogenically inactive and contain fat globules. They are commonly used to measure the insulin dependent stimulation of glycogen synthase activity, glucose incorporation into glycogen, and glucose transport. See Lin and Lawrence *JBC* 269(33):21255–61 (1994), Robinson and James, *Am J. Physiol.* 263:E383–93 (1992), and Shepherd et al, *Biochem Soc Trans* 23: 202s (1995).

L6 myocytes cell line displays the properties of a differentiated muscle cell. L6 myocytes have been used to measure the insulin-dependent stimulation of glycogen synthase activity, glucose incorporation into glycogen, and glucose transport. See Begum and Ragolia, *Endocrinology* 137:2441–6 (1996).

3. Assays Using Human Muscle Primary Myocytes

Assays using human muscle primary myocytes can be conducted as described above for cell-based assays generally. Ultimately, testing the ability of inhibitor compounds to stimulate glucose uptake in normal and diabetic human cells is important. Procedures for culturing and assaying cells from human muscle biopsies (HSMCs) have been developed indicating such an assay as the most physiologically relevant cell-based assay of insulin-stimulated effects in human cells, and allowing for measurement of glucose uptake and glycogen synthesis as described in Claraldi et al, *J. Clin. Invest.* 96:2820–7 (1995), Henry et al, *Diabetes* 44:936–46 (1995), and Henry et al, *Diabetes* 45:400–7 (1996). Compounds that stimulate insulin-dependent effects in differentiated cell lines will be tested in the HSMC system. Compounds that are successful in some or all of these assays described above are candidates for animal studies. Appropriate model systems for NIDDM in mice and rats are well documented as described in Leiter, *FASEB J* 3:2231–41(1989).

Candidate Inhibitors

Candidate inhibitors may be derived from almost any source of chemical libraries, naturally occurring compounds, or mixtures of compounds. Described below are some exemplary and possible sources of candidate inhibitors, synthesis of libraries of peptides, peptoids, and small organic molecules. The candidate inhibitors can also be polynucleotides, for example ribozymes or antisense molecules designed based on knowledge of GSK3 polynucleotide sequence.

The term "inhibitor" refers to any inhibitor or antagonist of GSK3 activity. The inhibitor of GSK3 can be a peptide GSK3 antagonist, a peptoid GSK3 antagonist, a small organic molecule GSK3 antagonist or a polynucleotide GSK3 antagonist. It is expected that some inhibitors will act at transcription, some at translation, and some on the mature protein, for example, at the specific site of GSK3 that acts to phosphorylate another protein. However, the use and appropriateness of such inhibitors of GSK3 for the purposes of the invention are not limited to any theories of mechanism of action of the inhibitor. It is sufficient for purposes of the invention that an inhibitor inhibit the activity of GSK3, for example, and most particularly, the kinase activity of GSK3.

Analogs of peptides as used herein include peptides having one or more peptide mimics, for example peptoids that possess protein-like activity. Included within the definition are, for example, peptides containing one or more analogs of an amino acid (including, for example, unnatural amino acids), peptides with substituted linkages, as well as other modifications known in the art, both naturally occurring and not naturally occurring.

The term "small molecule" includes any chemical or other moiety that can act to affect biological processes. Small molecules can include any number of therapeutic agents presently known and used, or can be small molecules synthesized in a library of such molecules for the purpose of screening for function. Small molecules are distinguished from polymers and macromolecules by size and lack of polymerization. Small molecules can include peptides, peptoids and small organic molecules.

The candidate inhibitors and libraries of candidate inhibitors for screening by the methods of the invention can be derived from any of the various possible sources of candidate inhibitors, such as for example, libraries of peptides, peptoids, small molecules, and polynucleotides. The polynucleotide libraries can include antisense molecules or ribozymes. The inhibitor could be a polypeptide presented by phage display, provided mechanisms are designed to get the polypeptide inhibitor into the cell, or the polypeptide inhibitor was used to construct an intrabody or intracellular antibody. In general a GSK3 inhibitor can be any molecule that may be capable of inhibiting GSK3 activity. Some libraries for screening can be subdivided into library pools for assaying inhibition of GSK3 activity by the method of the invention. Some of each pool is assayed and some is saved for reassay, or to further subdivide into subpools, should a positive be identified. Generation of some of the possible libraries suitable for assay by the methods of the invention is described herein.

Libraries that are peptide and peptoid inhibitors of GSK3 are made as follows. A "library" of peptides may be synthesized and used following the methods disclosed in U.S. Pat. No. 5,010,175, (the '175 patent) and in PCT WO91/17823. In the method of the '175 patent, a suitable peptide synthesis support, for example, a resin, is coupled to a mixture of appropriately protected, activated amino acids. The method described in WO91/17823 is similar but simplifies the process of determining which peptides are responsible for any observed alteration of gene expression in a responsive cell. The methods described in WO91/17823 and U.S. Pat. No. 5,194,392 enable the preparation of such pools and subpools by automated techniques in parallel, such that all synthesis and resynthesis may be performed in a matter of days.

Further alternative agents include peptide analogs and derivatives that can act as stimulators or inhibitors of gene expression, or as ligands or antagonists. Some general means contemplated for the production of peptides, analogs or derivatives are outlined in CHEMISTRY AND BIOCHEMISTRY OF AMINO ACIDS, PEPTIDES, AND PROTEINS—A SURVEY OF RECENT DEVELOPMENTS, Weinstein, B. ed., Marcell Dekker, Inc., publ. New York (1983). Moreover, substitution of D-amino acids for the normal L-stereoisomers can be carried out to increase the half-lives of the molecules.

Peptoids, polymers comprised of monomer units of at least some N-substituted moieties, can act as small molecule stimulators or inhibitors herein and can be synthesized as described in PCT 91/19735. Presently preferred amino acid substitutes are N-alkylated derivatives of glycine, which are easily synthesized and incorporated into polypeptide chains. However, any monomer units that allow for the sequence specific synthesis of pools of diverse molecules are appropriate for use in producing peptoid molecules. The benefits of these molecules for the purpose of the invention is that they occupy different conformational space than a peptide and are more resistant to the action of proteases because their amide linkages are N-substituted.

Peptoids are easily synthesized by standard chemical methods. The preferred method of synthesis is the "submonomer" technique described by R. Zuckermann et al., *J. Am. Chem. Soc.* 114:10646–7 (1992). Synthesis by solid phase techniques of heterocyclic organic compounds in which N-substituted glycine monomer units forms a backbone is described in copending application entitled "Synthesis of N-Substituted Oligomers" filed on Jun. 7, 1995 and is herein incorporated by reference in full. Combinatorial libraries of mixtures of such heterocyclic organic compounds can then be assayed for the ability to alter gene expression.

Synthesis by solid phase of other heterocyclic organic compounds in combinatorial libraries is also described in copending application U.S. Ser. No. 08/485,006 entitled "Combinatorial Libraries of Substrate-Bound Cyclic Organic Compounds" filed on Jun. 7, 1995, herein incorporated by reference in full. Highly substituted cyclic structures can be synthesized on a solid support by combining the submonomer method with powerful solution phase chemistry. Cyclic compounds containing one, two, three or more fused rings are formed by the submonomer method by first synthesizing a linear backbone followed by subsequent intramolecular or intermolecular cyclization as described in the same application.

Where the selected inhibitor of GSK3 is a ribozyme, for example, a ribozyme targeting a GSK3 gene, the ribozyme can be chemically synthesized or prepared in a vector for a gene therapy protocol including preparation of DNA encoding the ribozyme sequence. The synthetic ribozymes or a vector for gene therapy delivery can be encased in liposomes for delivery, or the synthetic ribozyme can be administered with a pharmaceutically acceptable carrier. A ribozyme is a polynucleotide that has the ability to catalyze the cleavage of a polynucleotide substrate. Ribozymes for inactivating a gene can be prepared and used as described in Long et al., *FASEB J.* 7:25 (1993), and Symons, *Ann. Rev. Biochem.* 61:641 (1992), Perrotta et al., *Biochem.* 31:16, 17 (1992); and U.S. Pat. No. 5,225,337, U.S. Pat. No. 5,168,053, U.S. Pat. No. 5,168,053 and U.S. Pat. No. 5,116,742, Ojwang et al., *Proc. Natl. Acad. Sci. USA* 89:10802–10806 (1992), U.S. Pat. No. 5,254,678 and in U.S. Pat. No. 5,144,019, U.S. Pat. No. 5,225,337, U.S. Pat. No. 5,116,742, U.S. Pat. No. 5,168,053. Preparation and use of such ribozyme fragments in a hammerhead structure are described by Koizumi et al., *Nucleic Acids Res.* 17:7059–7071 (1989). Preparation and use of ribozyme fragments in a hairpin structure are described by Chowrira and Burke, *Nucleic Acids Research* 20:2835 (1992).

The hybridizing region of the ribozyme or of an antisense polynucleotide may be modified by linking the displacement arm in a linear arrangement, or alternatively, may be prepared as a branched structure as described in Horn and Urdea, *Nucleic Acids Res.* 17:6959–67 (1989). The basic structure of the ribozymes or antisense polynucleotides may also be chemically altered in ways quite familiar to those skilled in the art. Chemically synthesized ribozymes and antisense molecules can be administered as synthetic oligonucleotide derivatives modified by monomeric units. Ribozymes and antisense molecules can also be placed in a vector and expressed intracellularly in a gene therapy protocol.

The invention includes generating cRNA and cDNA libraries for screening for inhibition of GSK3 activity, can require overexpression of recombinant GSK3, and can also involve transforming a cell with the gene for GSK3 for expression in the assay. However, it is not necessary to overexpress GSK3 in all the assays as GSK3 is endogenously expressed in almost all cells. For example the tau phosphorylation assay prescribes overexpression of GSK3, whereas the assays including the CHO-IR or HEPG2, 3T3-L1 or L6, or human muscle myoctye assays employ GSK3 endogenously expressed in the cell system being used. Exemplary systems for generating polypeptides or libraries useful for the method of the invention would include, for example, any standard or useful mammalian, bacterial, yeast or insect expression system, many of which are described in WO 96/35787. Thus any polypeptide or peptide useful in the invention can be made by these or other standard methods.

Other items not specifically exemplified, such as plasmids, can be constructed and purified using standard recombinant DNA techniques described in, for example, Sambrook et al. (1989), *MOLECULAR CLONING, A LABORATORY MANUAL*, 2d edition (Cold Spring Harbor Press, Cold Spring Harbor, N.Y.), and Ausubel et al., *CURRENT PROTOCOLS IN MOLECULAR BIOLOGY* (1994), (Greene Publishing Associates and John Wiley & Sons, New York, N.Y.) under the current regulations described in United States Dept. of *HHS, NATIONAL INSTITUTE OF HEALTH (NLH) GUIDELINES FOR RECOMBINANT DNA RESEARCH*. These references include procedures for the following standard methods: cloning procedures with plasmids, transformation of host cells, cell culture, plasmid DNA purification, phenol extraction of DNA, ethanol precipitation of DNA, agarose gel electrophoresis, purification of DNA fragments from agarose gels, and restriction endonuclease and other DNA-modifying enzyme reactions.

Pharmaceutical Compositions and Methods of Treatment

A GSK3 inhibitor identified from a library of candidates using one of the several methods of identification of selective GSK3 inhibitors of the invention described herein can be prepared as a pharmaceutical composition using a pharmaceutically acceptable carrier. The pharmaceutical composition including the selective GSK3 inhibitor can be administered to a subject having NIDDM, Alzheimer's, the potential for either disease, or having any other disorder mediated by GSK3 activity. Once a selective GSK3 inhibitor is shown to work in the stable tissue culture cells, appropriate formulations can be devised. In addition, preliminary pharmacokinetic and absorption studies can be done in preparation for the animal studies, which will ensue if the compounds are effective in the assays using human muscle primary myocytes.

"Therapeutically effective amount" as used herein refers to that amount that is effective to obtain the desired therapeutic result. The term "an effective amount" of an inhibitor of GSK3 refers to an amount that is effective to induce an inhibition of GSK3 activity. That activity can be GSK3 kinase activity. The inhibitory amount may be determined directly by measuring the inhibition of a GSK3 activity, or, for example, where the desired effect is an effect on an activity downstream of GSK3 activity in a pathway that includes GSK3, the inhibition may be measured by measuring a downstream effect. Thus, for example where inhibition of GSK3 results in the arrest of phosphorylation of glycogen synthase, the effects of the inhibitor may be effects on an insulin-dependent or insulin-related pathway, and the inhibitor may be administered to the point where glucose uptake is increased to optimal levels. Also, where the inhibition of GSK3 results in the absence of phosphorylation of a protein that is required for further biological activity, for example, the tau protein, then the inhibitor may be administered until polymerization of phosphorylated tau protein is substantially arrested. Therefore, the inhibition of GSK3 activity will depend in part on the nature of the inhibited pathway or process that involves GSK3 activity, and on the effects that inhibition of GSK3 activity has in a given biological context.

The amount of the inhibitor that will constitute an inhibitory amount will vary depending on such parameters as the inhibitor and its potency, the half-life of the inhibitor in the body, the rate of progression of the disease or biological condition being treated, the responsiveness of the condition to the dose of treatment or pattern of administration, the formulation, the attending physician's assessment of the medical situation, and other relevant factors, and in general the health of the patient, and other considerations such as prior administration of other therapeutics, or co-administration of any therapeutic that will have an effect on the inhibitory activity of the inhibitor or that will have an effect on GSK3 activity, or a pathway mediated by GSK3 activity. It is expected that the inhibitory amount will fall in a relatively broad range that can be determined through routine trials.

"Co-administration" as used herein means administration of an inhibitor of GSK3 according to the method of the invention in combination with a second therapeutic agent. The second therapeutic agent can be any therapeutic agent useful for treatment of the patient's condition. For example, inhibition of GSK3 with lithium as a second therapeutic agent used in conjunction with a therapeutic agent inhibitor of GSK3 is contemplated. Additionally, for example, a first therapeutic agent can be a small molecule inhibitor of GSK3 activity, and a second therapeutic agent can be an antisense or ribozyme molecule against GSK3 that, when administered in a viral or nonviral vector, will facilitate a transcriptional inhibition of GSK3 that will complement the inhibitory activity of the small molecule. The second therapeutic agent can also be lithium ion. Co-administration may be simultaneous, for example, by administering a mixture of the therapeutic agents, or may be accomplished by administration of the agents separately, such as within a short time period. Co-administration also includes successive administration of an inhibitor of GSK3 and one or more of another therapeutic agent. The second therapeutic agent or agents may be administered before or after the inhibitor of GSK3. The second therapeutic agent may also be an inhibitor of GSK3, which has particular advantages when administered with the first inhibitor. Dosage treatment may be a single dose schedule or a multiple dose schedule.

Administration of small molecule therapeutic agents will vary depending on the potency of the small molecule. For a very potent small molecule inhibitor, nanogram (ng) amounts per kilogram of patient, or microgram ($\mu$g) amounts per kilogram of patient may be sufficient. Thus, for small organic molecules, peptides, or peptoids, the dosage range can be for example, from about 100 ng/kg to about 500 mg/kg of patient weight, or the dosage range can be a range within this broad range, for example, about 100 ng/kg to 400.ng/kg, from about 500 ng/kg to about 1 $\mu$g/kg, from about 5 $\mu$g/kg to about 100 $\mu$g/kg, from about 150 $\mu$g/kg to about 500 $\mu$g/kg, from about 600 $\mu$g/kg to about 1 mg/kg, or from about 25 mg/kg, to about 500 mg/kg of patient weight.

The individual doses for viral gene delivery vehicles for delivery of polynucleotide inhibitors normally used are $10^7$ to $10^9$ c.f.u. (colony forming units of neomycin resistance titered on HTI1080 cells) per body. Dosages for adeno-associated virus (AAV) containing delivery systems are in the range of about $10^9$ to about $10^{11}$ particles per body. Dosages for nonviral gene delivery vehicles for delivering polynucleotide inhibitors of GSK3 are described for example in U.S. Pat. No. 5,589,466 and U.S. Pat. No.

5,580,859. Dosage of nonviral gene delivery vehicles can be 1 μg, preferably at least 5 or 10 μg, and more preferably at least 50 or 100 μg of polynucleotide, providing one or more dosages.

Non-coding sequences that act by a catalytic mechanism, for example, catalytically active ribozymes, may require lower doses than non-coding sequences that are held to the restrictions of stoichiometry, for example, antisense molecules, although expression limitations of the ribozymes may again raise the dosage requirements of ribozymes being expressed in vivo in order to achieve efficacy in the patient. Factors such as method of action and efficacy of transformation and expression are therefore considerations that will effect the dosage required for ultimate efficacy for polynucleotides. Where greater expression is desired, over a larger area of tissue, larger amounts of DNA or the same amounts readministered in a protocol of successive administrations, or several administrations to different adjacent or close tissue portions may be required to effect a positive therapeutic outcome.

In all cases, routine experimentation in clinical trials will determine specific ranges for optimal therapeutic effect, for each therapeutic and each administrative protocol, and administration to specific patients will also be adjusted to within effective and safe ranges depending on the patients' condition and responsiveness to initial administrations.

All of the therapeutic agents discovered by the methods of the invention can be incorporated into an appropriate pharmaceutical composition that includes a pharmaceutically acceptable carrier for the agent. The pharmaceutical carrier for the agents may be the same or different for each agent. Suitable carriers may be large, slowly metabolized macromolecules such as proteins, polysaccharides, polylactic acids, polyglycolic acids, polymeric amino acids, amino acid copolymers, and inactive viruses in particles. Such carriers are well known to those of ordinary skill in the art. Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in REMINGTON'S PHARMACEUTICAL SCIENCES (Mack Pub. Co., N.J. 1991). Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier. Liposomes are described in U.S. Pat. No. 5,422,120 and 4,762,915, WO 95/13796, WO 94/23697, WO 91/144445 and EP 524,968, and in Starrier, *Biochemistry*, pages 236–240 (1975) W. H. Freeman, San Francisco, Shokai, *Biochem. Biophys. Acct.* 600:1 (1980); Bayer, *Biochem Biophys Acct* 550:464 (1979); Rivet, *Meth. Enzyme.* 149:119 (1987); Wang, *Proc. Natl. Acad. Sci.* 84:7851 (1987); and Plant, *Anal Biochem* 176:420 (1989).

The pharmaceutically acceptable carrier or diluent may be combined with other agents to provide a composition either as a liquid solution, or as a solid form (e.g., lyophilized) which can be resuspended in a solution prior to administration. The composition can be administered by parenteral or nonparenteral routes. Parenteral routes can include local injection into an organ or space of the body or systemic injection including intravenous, intraarterial injections or other systemic routes of administration. Nonparenteral routes can include oral administration.

The subject to be treated by the method of the invention should be diagnosed with a biological condition mediated by GSK3 activity. The term "biological condition" as used herein refers to a particular state of molecular and cellular systems in a biological context. A biological context includes any organism considered to have life, and for the purposes of this invention includes but is not limited to the following organisms: animals, mammals, humans, invertebrates and vertebrates. A biological condition can include, for example, a disease or a medical condition that may or may not be characterized by identifiable symptoms or indicators. The term "biological condition mediated by GSK3 activity" as used herein refers to any biological or medical condition or disorder in which GSK3 activity is identified, whether at normal or abnormal levels. The GSK3 activity mediates activity causing or related to causes of the biological or medical condition that causes the patient to seek medical attention. For example, such activity of GSK3 can be phosphorylation of glycogen synthase in the case of NIDDM, or hyperphosphorylation of the tau protein in the case of Alzheimer's disease. The condition or disorder may be caused by the GSK3 activity or may simply be characterized by GSK3 activity. That the condition is mediated by GSK3 activity means that some aspect of the condition can be traced to the GSK3 activity. By using the methods of treatment of the invention, inhibiting the GSK3 activity will then prevent, ameliorate or treat the condition so characterized. The term "susceptible to such condition" as used herein refers to prophylactic administration of a GSK3 inhibitor to a patient who is at risk for developing a condition mediated by GSK3 activity. Such a subject might be a person experiencing some pre-symptomatic indications of NIDDM or Alzheimer's.

EXAMPLES

The following examples are exemplary only, and are not intended to limit the invention.

Example 1

Assay of Phosphorylation of GSK3 Peptide Substrate

One possible method for screening for an inhibitor of GSK3 involves a kinase assay in which the kinase activity of GSK3 is measured in the presence of a candidate inhibitor. The assay relies on the ability of GSK3 to phosphorylate a substrate in the absence of an inhibitor. This example demonstrates the success of the claimed substrate in accomplishing this function.

A GSK3β gene was created in which a haemagluttinin (HA) epitope was fused to the N-terminal end of the GSK3β open reading frame in plasmid vector pCG, a pEVRF derivative, described in Giese et al. *Genes & Development* (1995) 9:995–1008, and in Matthias et al., *Nucleic Acids Res.* (1989) 17: 6418. pCG has a modified polylinker, and directs expression in mammalian cells from the human cytomegalovirus promoter/enhancer region. The resulting plasmid is pCG-HA-GSK3β. pCG-HA-GSK3β was transiently transfected into COS cells on 10 cm tissue culture plates using DEAE-Dextran, as described in Ausubel et al (1994) CURRENT PROTOCOLS IN MOLECULAR BIOLOGY, (Greene Publishing Associates and John Wiley & Sons, New York, N.Y.).

The final density of cells was 70% confluent and these cells were lysed in 700 µl Triton lysis buffer (20 mM TrisHCl pH7.9, 137mM NaCl, 1.0% Triton X-100, 10% glycerol, 1 mM NaVO$_3$, 20 mM NaF, 30 mM pNpp, 15 mM PP$_i$). Anti-HA antibody (12CA5 monoclonal antibody purchased from Boehringer Mannheim, Indianapolis, Ind.) was added to 300 µl of this lysate to a final concentration of 4 µg/ml and incubated for 1 h at 40° C. 100 µl of a 50% slurry of protein A-Sepharose® beads was added for 2 h at 4° C.

The beads were pelleted by centrifugation for 10 seconds in a microcentrifuge and washed with 0.5M LiCl, 0.5% Triton X-100, twice with phosphate buffered saline (PBS) and once with 10 mM TrisHCl pH 7.5, 5 mM MgCl$_2$, 1 mM DTT. All wash buffers contained 1 mM NaVO$_3$ and 25 mM β-glycerolphosphate. 33 µl of the beads were analysed by SDS-PAGE and western blotting with anti-HA antibody (12CA5 monoclonal antibody purchased from Boehringer Mannheim, Indianapolis, Ind.) to quantitate the amount of HA-GSK3β present.

The remaining 17 µl of beads was assayed according to the protocol of Wang et al, *Anal Biochem* 220: 397–402 (1994). To each 17 µl of pellet was added 3 µl 10× GSK buffer (100 mM MgCl$_2$, 20 mM DTT, 3M TrisHCl pH7.5), 0.7 µl CREB peptide (either prephosphorylated or non-prephosphorylated, 5 mg/ml, Chiron Mimotopes Peptide Systems, San Diego, Calif.), 0.3 µl 10 mM rATP, 1 µl g$^{32}$P-ATP (6000 Ci/mmol), 0.06 µl 5 mg/ml of protein kinase inhibitor (a protein kinase-A inhibitor or PKI), and 25 µl H$_2$O. The reaction was allowed to proceed for 20 minutes at 22° C. and then was stopped with 8 µl 500 mM EDTA. 22 µl of each reaction was spotted onto P81 phosphocellulose filter paper (purchased from Gibco-BRL Life Technologies, Gaithersburg, Md.) and washed 4 times for 5 minutes in 75 mM H$_3$PO$_4$. The filter papers were then assayed in a scintillation counter. Filter papers from experiments using the prephosphorylated CREB peptide substrate yielded counts of 85,000±5,000 cpm/min, whereas filter papers from experiments using the non-prephosphorylated CREB peptide substrate yielded counts of 5,000±1,000 cpm/min. The results indicated that the substrate was phosphorylated by GSK3 in the absence of an inhibitor, although the control substrate was not phosphorylated. This experiment demonstrates the specificity of the claimed peptide as a GSK3 substrate.

Example 2

Screening a Peptide Library of Random Hexamers for An Inhibitor of GSK3

A library of random hexamers can be purchased from Chiron Mimotopes, Clayton, Australia, or, alternatively a set of mixtures of random hexamers can be prepared by the method of either U.S. Pat. No. 5,010,175 or U.S. Pat. No. 5,194,392. For example, hexamers of the formula D1D2-XXXX, where D1 can equal any one of the 20 amino acids, and D2 can equal any one of the 20 amino acids, to yield a library of 400 possible hexamers are used; X is any amino acid, and the amino acid character of X is not controlled. Pools of this library are created and screened for an inhibitor by a kinase assay using purified GSK3 and the GSK3 phosphorylatable substrate the CREB peptide prephosphorylated at the C terminal serine. Positives are identified and the identity of D1 and D2 are determined for those positives. Further hexamers are resynthesized with the formula D1D2D3D4-XX, where D3 and D4 are one of the 20 amino acids, and D1 and D2 are established amino acids. Thus, another 400 random hexamers are screened and the positives identified and the identity of D3 and D4 determined. One more round of the screening ensues to identify a D5 and D6 amino acid for the positive hexamer. Once the positive hexamer sequence is determined, the inhibitor hexamer is tested in a fly eye in vivo screen for its ability to enhance the rough cell morphology of the eyes of a GSK3 inhibitory protein expressing transgenic fly, indicating a functional non-toxic inhibitor that crosses the cell surface.

Example 3

Cell-Based Assay for GSK3 Inhibitor

A small molecule GSK3 inhibitor is synthesized in sufficient quantities for cell-based assays. In a cell-based assay in Drosophila cells, the compound is tested for inhibition of GSK3 at an inhibitor concentration up to that at which it remains soluble in the culture medium. A positive result in this assay indicates that the inhibitor can enter cells and inhibit intracellular GSK3.

The inhibitor is then tested in a stable tissue culture cell assay in CHO-IR cells. An inhibitor that can function and exhibit a positive result in a stable tissue culture cell assay is then tested in a differentiated cell line using NIH 3T3-L1 adipocytes. An assay using this cell line will determine whether the GSK3 inhibitor can potentiate an insulin independent stimulation of glycogen synthase activity and glucose incorporation into glycogen, and glucose transport. Tests in human muscle primary myocytes are then conducted to determine whether the GSK3 inhibitor stimulates glucose uptake in normal and diabetic human cells.

Example 4

Treating a Patient with NIDDM

A patient is diagnosed in the early stages of non-insulin dependent diabetes mellitus. A small molecule inhibitor of GSK3 is formulated in an enteric capsule. The patient is directed to take one tablet after each meal for the purpose of stimulating the insulin signaling pathway, and thereby controlling glucose metabolism to levels that obviate the need for administration of exogenous insulin.

Example 5

Treating a Patient with Alzheimer's Disease

A patient is diagnosed with Alzheimer's disease. The patient is administered a selective small molecule inhibitor of GSK3-mediated tau hyperphosphorylation prepared in a formulation that crosses the blood/brain barrier. The patient is monitored for tau phosphorylated polymers by periodic analysis of proteins isolated from the patient's brain cells for the presence of phosphorylated forms of tau on an SDS-PAGE gel known to characterize the presence of and progression of the disease. The dosage of the inhibitor is adjusted as necessary to reduce the presence of the phosphorylated forms of tau protein.

What is claimed is:

1. A method for treating a biological condition mediated by glycogen synthase kinase 3 (GSK3) activity, said method comprising administering an effective amount of a pharmaceutical composition comprising a selective GSK3 inhibitor identified by:
   (a) contacting a first aliquot of a peptide substrate comprising SEQ ID NO:2, where the N-terminal serine is the target of phosphorylation by GSK3 and the C-terminal serine is prephosphorylated, coupled to an anchor ligand with GSK3 in the presence of radiolabeled phosphate-γATP, a substrate anchor, and a candidate inhibitor,
   (b) measuring a first incorporation of radiolabel into said peptide substrate,
   (c) contacting a second aliquot of said peptide substrate coupled to an anchor ligand with GSK3 in the presence of radiolabeled phosphate-γATP, and a substrate anchor,
   (d) measuring a second incorporation of radiolabel into said peptide substrate, and
   (e) identifying an inhibitor of GSK3 kinase activity by a reduction of radiolabel incorporation in step (b) compared to step (d),
to a subject having a condition mediated by GSK3 activity or susceptible to such a condition.

2. The method of claim 1, wherein said biological condition is non-insulin dependent diabetes mellitus (NIDDM).

3. The method of claim 1, wherein said biological condition is Alzheimer's disease.

4. The method of claim 1, wherein said selective inhibitor of GSK3 activity comprises an inhibitor selected from the group consisting of a small organic molecule, a peptide, and a peptoid.

5. The method of claim 1, further comprising administration of a second therapeutic agent.

6. The method of claim 5, wherein said second therapeutic agent is lithium ion.

7. A method of treating a subject having non-insulin dependent diabetes mellitus (NIDDM) or Alzheimer's disease, said method comprising administering a pharmaceutical composition comprising a pharmaceutically acceptable carrier and an effective amount of a selective inhibitor of GSK3 activity identified by:
   (a) contacting a first aliquot of a peptide substrate comprising SEQ ID NO:2, where the N-terminal serine is the target of phosphorylation by GSK3 and the C-terminal serine is prephosphorylated, coupled to an anchor ligand with GSK3 in the presence of radiolabeled phosphate-γATP, a substrate anchor and a candidate inhibitor,
   (b) measuring a first incorporation of radiolabel into said peptide substrate,
   (c) contacting a second aliquot of said peptide substrate coupled to an anchor ligand with GSK3 in the presence of radiolabeled phosphate-γATP, and a substrate anchor,
   (d) measuring a second incorporation of radiolabel into said peptide substrate, and
   (e) identifying an inhibitor of GSK3 kinase activity by a reduction of radiolabel incorporation in step (b) compared to step (d), to said subject, wherein said inhibitor is a small molecule.

8. A method of promoting activation of an insulin signaling pathway, said method comprising contacting a cell characterized by insulin resistance with an effective amount of a selective inhibitor of GSK3 identified by:
   (a) contacting a first aliquot of a peptide substrate comprising SEQ ID NO:2, where the N-terminal serine is the target of phosphorylation by GSK3 and the C-terminal serine is prephosphorylated, coupled to an anchor ligand with GSK3 in the presence of radiolabeled phosphate-γATP, a substrate anchor, and a candidate inhibitor,
   (b) measuring a first incorporation of radiolabel into said peptide substrate,
   (c) contacting a second aliquot of said peptide substrate coupled to an anchor ligand with GSK3 in the presence of radiolabeled phosphate-γATP, and a substrate anchor,
   (d) measuring a second incorporation of radiolabel into said peptide substrate, and
   (e) identifying an inhibitor of GSK3 kinase activity by a reduction of radiolabel incorporation in step (b) compared to step (d).

9. The method of claim 8, wherein said selective inhibitor of GSK3 is a small molecule.

10. A method of reducing tau hyperphosphorylation and polymerization in a population of cells exhibiting tau polymerization, said method comprising contacting said cells with an effective amount of a selective inhibitor of GSK3 identified by:
   (a) contacting a first aliquot of a peptide substrate comprising SEQ ID NO:2, where the N-terminal serine is the target of phosphorylation by GSK3 and the C-terminal serine is prephosphorylated, coupled to an anchor ligand with GSK3 in the presence of radiolabeled phosphate-γATP, a substrate anchor, and a candidate inhibitor,
   (b) measuring a first incorporation of radiolabel into said peptide substrate,
   (c) contacting a second aliquot of said peptide substrate coupled to an anchor ligand with GSK3 in the presence of radiolabeled phosphate-γATP, and a substrate anchor,
   (d) measuring a second incorporation of radiolabel into said peptide substrate, and
   (e) identifying an inhibitor of GSK3 kinase activity by a reduction of radiolabel incorporation in step (b) compared to step (d).

11. The method of claim 10, wherein said selective inhibitor of GSK3 is a small molecule.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 17 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:1:

Ser Gly Ser Gly Lys Arg Arg Glu Ile Leu Ser Arg Arg Pro Ser Tyr
1               5                   10                  15

Arg (2) INFORMATION FOR SEQ ID NO:2:

(i) SEQUENCE CHARACTERISTICS:
       (A) LENGTH: 5 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:2:

Ser Xaa Xaa Xaa Ser
1               5